(12) United States Patent
Ortiz et al.

(10) Patent No.: US 8,012,086 B2
(45) Date of Patent: Sep. 6, 2011

(54) STERILE TRANSCOLONIC ACCESS DEVICE (75) Inventors: Mark S. Ortiz, Milford, OH (US); Ragae M. Ghabrial, Cincinnati, OH (US); William D. Fox, New Richmond, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 588 days.

(21) Appl. No.: 11/550,922

(22) Filed: Oct. 19, 2006

(65) Prior Publication Data

US 2008/0097157 A1     Apr. 24, 2008

(51) Int. Cl.
*A61B 1/00* (2006.01)
*A61B 1/04* (2006.01)
*A61B 1/06* (2006.01)

(52) U.S. Cl. .......................... 600/184; 600/115; 600/170

(58) Field of Classification Search .................. 606/194, 606/170, 167, 159; 600/104, 109, 112, 114, 600/117, 121, 123, 133, 136, 184, 204, 208, 600/205, 170, 171, 172, 160, 115, 116, 564, 600/567, 571; 604/22, 48, 93.01, 171, 167.01, 604/167.02, 173, 174, 176, 170.03, 164.01–164.03, 604/164.09, 107, 268, 326
See application file for complete search history.

(56) References Cited

U.S. PATENT DOCUMENTS

| | | | |
|---|---|---|---|
| 3,995,617 A * | 12/1976 | Watkins et al. | 600/16 |
| 4,224,929 A * | 9/1980 | Furihata | 600/116 |
| 5,287,857 A * | 2/1994 | Mann | 600/566 |
| 5,297,536 A | 3/1994 | Wilk | |
| 5,458,112 A * | 10/1995 | Weaver | 600/566 |
| 5,458,131 A | 10/1995 | Wilk | |
| 5,672,153 A | 9/1997 | Lax et al. | |
| 5,964,223 A * | 10/1999 | Baran | 128/207.14 |
| 6,030,365 A | 2/2000 | Laufer | |
| 6,129,713 A * | 10/2000 | Mangosong et al. | 604/264 |
| 6,383,198 B1 * | 5/2002 | Hamilton | 606/115 |
| 6,390,988 B1 * | 5/2002 | Robinson | 600/531 |
| 6,517,477 B1 * | 2/2003 | Wendlandt | 600/114 |
| 6,632,227 B2 * | 10/2003 | Adams | 606/110 |
| 6,786,887 B2 * | 9/2004 | Roychowdhury et al. | 604/96.01 |
| 6,918,871 B2 | 7/2005 | Schulze | |
| 6,923,754 B2 * | 8/2005 | Lubock | 600/3 |
| 2001/0049497 A1 | 12/2001 | Kalloo et al. | |

(Continued)

FOREIGN PATENT DOCUMENTS

WO    WO 01/54568 A    8/2001

(Continued)

OTHER PUBLICATIONS

International Search Report mailed May 2, 2008 for International Application PCT/US2007/081741 (8 pages).

*Primary Examiner* — Anhtuan T Nguyen
*Assistant Examiner* — Jocelin C Tanner (57) ABSTRACT

Devices and methods useful for transluminally accessing a body cavity are disclosed. In one embodiment, a transluminal access device adapted to be inserted through a body lumen is provided and can include an inner shaft having an opening at its distal end and adapted to be positioned adjacent to an inner wall of a body lumen. The inner shaft can include one or more sealing mechanisms, such as one or more seals with suction ports formed thereon for isolating a portion of a body lumen. The isolated portion may be sterilized and serve as an access point or otomy site for penetrating the wall of the body lumen to access a body cavity.

21 Claims, 5 Drawing Sheets

U.S. PATENT DOCUMENTS

| | | |
|---|---|---|
| 2003/0225312 A1 | 12/2003 | Suzuki et al. |
| 2003/0229296 A1 | 12/2003 | Ishikawa et al. |
| 2005/0090709 A1 | 4/2005 | Okada et al. |
| 2005/0101837 A1 | 5/2005 | Kalloo et al. |
| 2005/0107664 A1 | 5/2005 | Kalloo et al. |
| 2005/0165329 A1* | 7/2005 | Taylor et al. ................. 600/566 |
| 2005/0272977 A1 | 12/2005 | Saadat et al. |
| 2005/0277945 A1 | 12/2005 | Saadat et al. |
| 2006/0178562 A1 | 8/2006 | Saadat et al. |
| 2006/0241344 A1 | 10/2006 | Wilk |
| 2007/0287886 A1* | 12/2007 | Saadat ......................... 600/115 |

FOREIGN PATENT DOCUMENTS

| | | |
|---|---|---|
| WO | WO 2005/000111 A | 1/2005 |

* cited by examiner

STERILE TRANSCOLONIC ACCESS DEVICE

FIELD OF THE INVENTION

The present invention generally relates to surgical methods and devices, and in particular to methods and devices for obtaining transluminal access to a body cavity.

BACKGROUND OF THE INVENTION

Surgery through a natural orifice poses a number of challenges over laparoscopy or open surgery. Where the surgery is purely endoscopic, i.e., strictly through a natural orifice, the surgeon faces the upfront challenge of gaining adequate access to the desired operative site in the body. For example, many types of surgery require access to the peritoneum. The surgeon may reach the desired location by penetrating the wall of a body lumen, such as a lumen of the gastrointestinal tract. For example, in a transanal procedure the surgeon typically creates a passageway through the wall of the colon to access the peritoneal cavity. Similarly, in a transoral or transgastric procedure the surgeon can create a passageway through the stomach.

Such procedures often involve creating a sterile access point or section of lumen (e.g., an otomy site) at which to penetrate the lumen wall. Because the otomy site and the peritoneal cavity, or other body cavity, can become inflamed and/or infected from microbial or other contamination, sterilization is often of utmost concern. Such concerns are heightened when accessing the peritoneum from the colon. At the same time, the surgeon performing natural orifice surgery faces a significant loss of dexterity and feel, and reduced ability to maneuver surgical tools and devices. Ideally, the access devices and techniques employed by the surgeon can provide a stable and secure transluminal access point through which to operate, and do not unduly hinder the already difficult manipulation of surgical tools and devices into and within the body cavity.

Accordingly, there is a need in the art for novel methods and devices for providing access to a body cavity through the wall of a body lumen. There is also a need for devices and methods that can facilitate the sterilization of a local portion of a body lumen for use as an access point or otomy site for penetration of the wall of the body lumen.

SUMMARY OF THE INVENTION

Devices and methods for transluminally accessing a body cavity are disclosed. The devices and methods have particular applicability in natural orifice surgery. In one exemplary embodiment, a transluminal access device is provided and can include an inner shaft that is adapted to be inserted through a body lumen. The inner shaft can have a proximal end, a distal end, and an inner lumen extending therethrough. The distal end can include an opening adapted to be positioned adjacent to an inner wall of the body lumen. In an exemplary embodiment, the opening is formed in a sidewall of the inner shaft. The device can also include an expandable member disposed around the opening and adapted to stabilize the opening relative to a tissue surface.

In another embodiment, the device can include a sealing mechanism that is at least partially disposed around the inner shaft and that is adapted to isolate the opening within a portion of the body lumen containing the inner shaft. In one exemplary embodiment, the sealing mechanism is coupled to a distal portion of an outer shaft that is disposed around at least a portion of the inner shaft. For example, the sealing mechanism can include a first annular seal that is positioned distal of the opening and that is formed on a distal tip coupled to a distal end of the outer shaft, and a second annular seal that is positioned proximal of the opening and that is formed on the distal end of the outer shaft. The first and second annular seals can be adapted to form a seal around an inner wall of a body lumen. While various sealing techniques could be used, in one embodiment, the first and second annular seals can each include a plurality of suction ports that are formed around an outer perimeter thereof and that are adapted to suction tissue onto the first and second annular seals. In another embodiment, the distal tip can be coupled to the distal end of the outer shaft by one or more struts extending therebetween. An optical viewing instrument can also be associated with the distal tip.

In another embodiment, a transluminal access system is provided and includes an outer shaft having proximal and distal ends with an inner lumen extending therethrough. The outer shaft can be adapted to be inserted through a body lumen, and it can optionally have an optical viewing instrument associated with it. The system can also include an access element extending from the distal end of the outer shaft and having at least one opening formed therein. The access element can be adapted to be positioned adjacent to an inner wall of a body lumen. In one embodiment, the access element can be in the form of an inner shaft extending through the outer shaft. The opening can be formed in a sidewall of the inner shaft adjacent to a distal end of the inner shaft. In certain embodiments, the opening can have an expandable member disposed around it that is adapted to stabilize the opening relative to a tissue surface. In another embodiment, at least a portion of the outer shaft and the access element can be flexible to allow the outer shaft and access element to be inserted through a tortuous lumen.

In yet other aspects, the system can include a first annular seal coupled to the outer shaft and positioned distal of the opening. The first annular seal can be adapted to form a seal with or around an inner wall of a body lumen. The system can also include a second annular seal coupled to the outer shaft and positioned proximal of the opening. The second annular seal can be adapted to form a seal with or around an inner wall of a body lumen. The first and second annular seals can each include a plurality of suctions ports formed around an outer perimeter thereof for suctioning tissue onto the first and second annular seals. In an exemplary embodiment, the first annular seal is formed on a distal tip coupled to and spaced apart from the distal end of the outer shaft, and the second annular seal is disposed around the distal end of the outer shaft. The distal tip can be capped to prevent fluid flow therethrough.

Methods for accessing a body cavity are also provided herein. In one embodiment an exemplary method includes positioning an access port located on a distal end of an inner shaft adjacent to an inner wall of a body lumen. The access port can be formed in a sidewall of the inner shaft and it can face an inner wall of the body lumen. In some cases, positioning the access port can involve advancing the inner shaft through a colon. The method can also include isolating a section of the body lumen containing the access port from a remainder of the body lumen. The isolation can involve forming a first seal with the inner wall of the body lumen at a location distal to the access port, and forming a second seal with the inner wall of the body lumen at a location proximal to the access port. The first and second seals can be formed by suctioning the inner wall of the body lumen using an annular sealing mechanism. In an exemplary embodiment, the first seal is formed around an outer surface of a distal tip that is adapted to prevent fluid flow therethrough, and the second seal is formed around an outer shaft disposed around the inner shaft. The method can also include sterilizing the isolated section of the body lumen. The sterilization can optionally be performed by introducing an irrigation fluid through the outer shaft. In a further embodiment, the method can include penetrating through the inner wall of the body lumen to provide access through the access port to a body cavity positioned adjacent to the body lumen.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention generally provides devices and methods useful for accessing a body cavity, particularly by gaining access transluminally, i.e., through a body lumen. As such, in many cases the methods and devices can be employed to create a pathway from the exterior of the body to a desired operative site within the body. The devices and methods are also useful for isolating and/or sterilizing an area within a body lumen to provide sterile access to a body cavity located outside of the body lumen. Although many of the embodiments disclosed herein will be described in the context of accessing the peritoneal cavity from the intestine and particularly from the colon, such descriptions are by way of example only and the devices and methods disclosed herein are not limited in applicability to such applications. They may be used in natural orifice surgeries, endoscopic and non-endoscopic procedures, transcolonic, transoral, and transgastric applications, and virtually any other medical procedure now or later in use. Furthermore, they may be used to access body cavities other than the peritoneum or other organs adjacent to a body lumen or even to perform surgery on the inner wall of the body lumen itself rather than facilitating access through the lumen wall.

Figure 1:
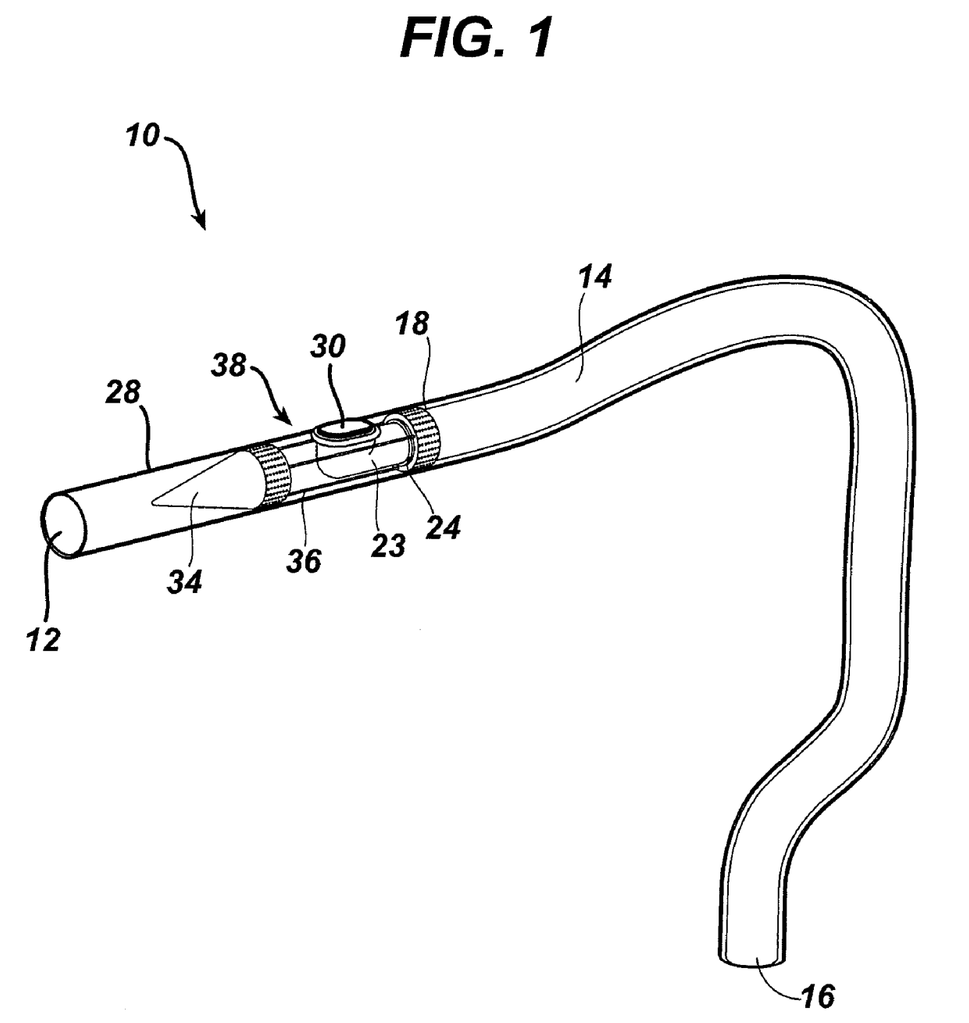
FIG. 1 is a perspective view of one exemplary embodiment of a transluminal access device shown contained within the colon.
Figure 2:
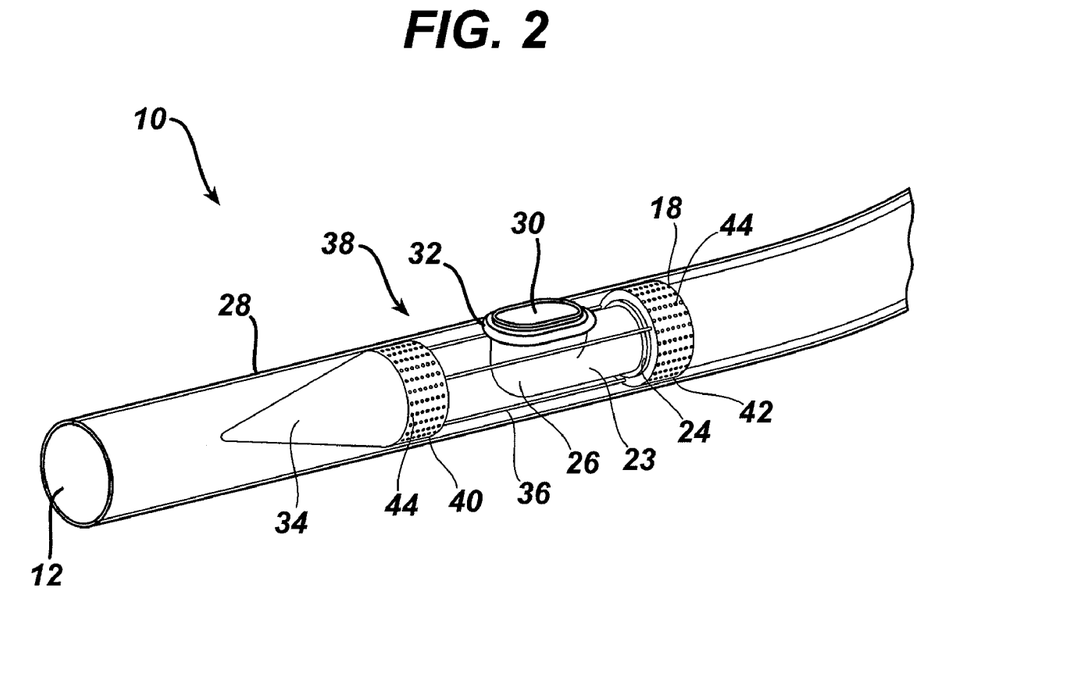
FIG. 2 is an enlarged perspective view of a distal portion of the device shown in FIG. 1 contained within the colon.

FIGS. 1-2 illustrate one exemplary embodiment of a translumenal access device 10 disposed within a body lumen 12 that is generally in the shape of the colon. The illustrated device 10 generally includes an outer shaft 14 with a proximal end 16 and a distal end 18. The outer shaft 14 can have two seals, a first seal 42 disposed on the distal end 18 of the outer shaft 14, and a second seal 40 disposed on a distal tip 34 attached to the outer shaft 14. Each seal 40, 42 can attach to the inner wall 28 of the body lumen 12, isolating a section of the body lumen 12 located between the seals 40, 42. To facilitate the introduction of surgical materials or tools to the isolated region, the access device 10 can also include a hollow inner shaft 23 extending therethrough and having a port or opening 30 positioned between the seals 40, 42 on the outer shaft 14. The opening 30 can be used to sterilize the isolated portion of the body lumen 12 (for example, by an antiseptic wash passed through the opening 30 or using other known sterilization techniques) and/or to access a body cavity through the inner wall 28 of the body lumen 12. Sterilizing the isolated region prior to gaining access to a body is particularly advantageous as it will prevent bacteria, such as flora, from being carried into the body cavity.

Figure 3:
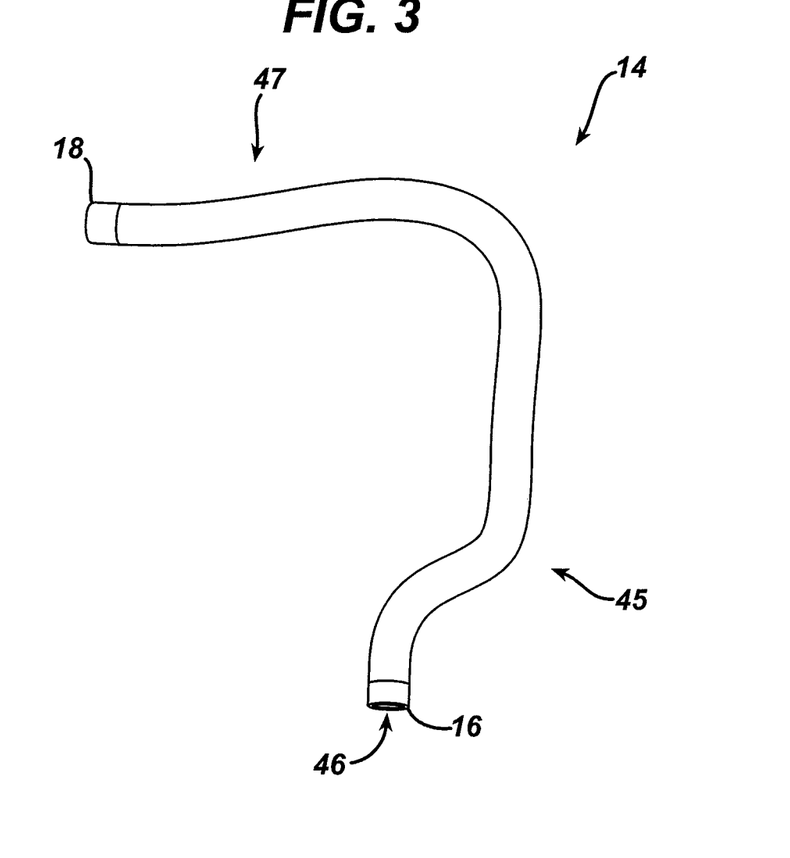
FIG. 3 is a side view of an outer shaft of the device shown in FIG. 1.
Figure 3A:
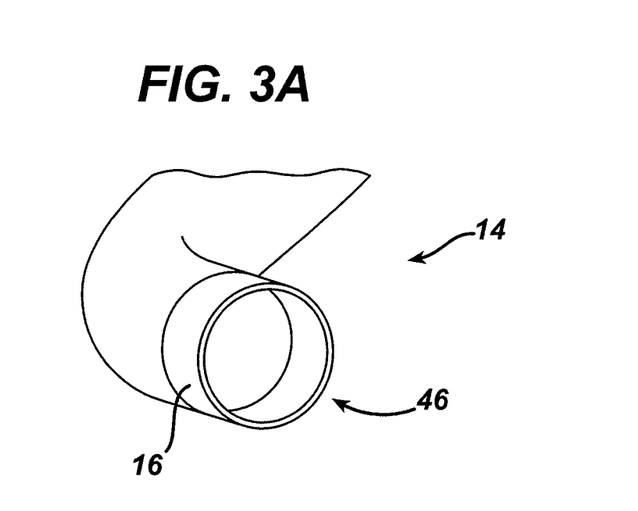
FIG. 3A is a perspective view of the proximal end of the outer shaft of FIG. 3.

The outer shaft 14 can have a variety of configurations, but in an exemplary embodiment the outer shaft 14 includes a proximal end 16 adapted to remain outside of the body, and a distal end 18 adapted to be positioned within the body and adjacent to a surgical site. As such, it can have virtually any length as necessary for the application. Where the device 10 is used for endoscopic procedures, the outer shaft 14, or portions thereof, can be flexible to facilitate insertion through a tortuous body lumen. For example, it may be advantageous in some cases for a distal portion 47 of the outer shaft 14 to be flexible while a proximal portion 45 of the outer shaft 14—for example corresponding to a portion that protrudes from a natural orifice—is rigid. Alternatively the outer shaft 14 can include articulating segments placed along its length or in desired locations or intervals in order to provide a desired degree of suppleness. The outer shaft 14 can also have a circular or approximately circular cross-sectional shape (as seen in FIG. 3A), in order to aid insertion of the shaft 14 into a body lumen 12. However, virtually any shape, including elliptical, oval, square, rectangular, and so on, can be used, as one of ordinary skill will recognize. One or more inner lumens 46 can also extend through the outer shaft 14. FIG. 3A illustrates an inner lumen 46 extending through the outer shaft 14 for providing access or serving as a passageway through the outer shaft 14 for one or more surgical devices, tools, materials, fluids, antiseptic agents, and the like. If the outer shaft 14 has a plurality of inner lumens 46 formed therethrough, each lumen may be used for a different tool, material, or fluid, or to transmit a suction force, and so on.

The outer shaft 14 can also have an opening or cut-out formed in a sidewall adjacent to the distal end 18 to provide access to the body lumen 12. In the illustrated embodiment shown in FIG. 1, the outer shaft 14 has a distal tip 34 spaced apart from but attached to the distal end 18 of the outer shaft 14 such that an open region 38 is formed between the distal end 18 of the outer shaft 14 and the distal tip 34. The distal tip 34 can act as a cap or a seal against the body lumen 12, and can also aid or guide the insertion of the device 10 into the colon or other body lumen 12, as will be discussed below. The distal tip 34 can have a variety of configurations. As shown in FIG.

Figure 4:
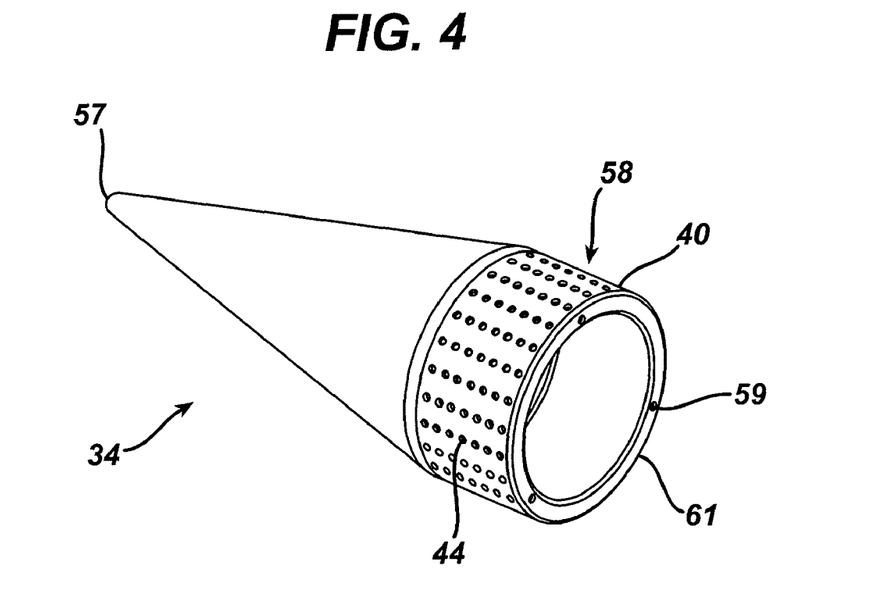
FIG. 4 is a perspective view of a distal tip of the device shown in FIGS. 1 and 2.

4, the distal tip 34 has a conical shape with a tapered distal end 57, although the distal tip 34 can also have a tip that is pointed, semi-spherical, frustrum-shaped, symmetrical, or asymmetrical. In addition, the distal tip 34 can have incorporated into it an optical viewing device such as a camera or fiber optic element, which can guide the insertion and advancement of the device 10. The same or a different optical viewing device can also be positioned in the distal tip 34 for viewing the inner wall 28 of the body lumen 12 adjacent the open region 38 formed in the outer shaft 14. An optical viewing device so positioned can aid the user in placing the device within the body lumen 12, penetrating the inner wall 28 of the body lumen 12, and/or in performing other procedures.

Figure 5:
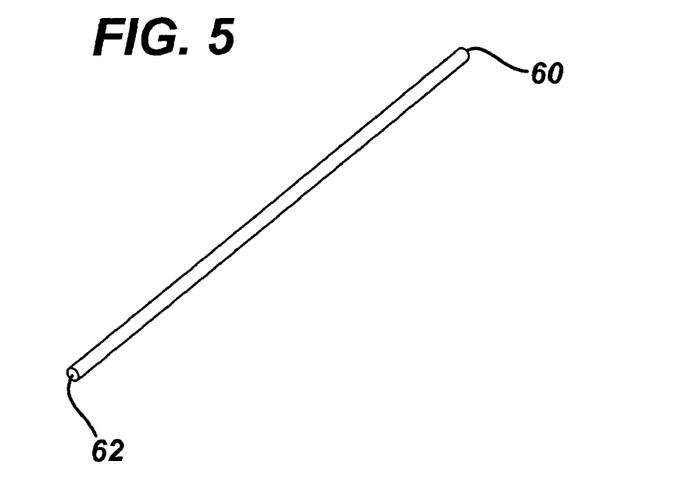
FIG. 5 is perspective view of a strut of the device shown in FIGS. 1 and 2.

The distal tip 34 can be attached to or coupled to the distal end 18 of the outer shaft 14 using a variety of techniques. In the illustrated embodiment, the distal tip 34 is attached to the distal end 18 of the outer shaft 14 by one or more connecting or support members. The connecting or support member can have any number of forms, but as shown in FIG. 5 the device 10 includes struts 36, such as solid rods, each having a proximal end 60 coupled to the distal end 18 of the outer shaft 14, and a distal end 62 coupled to a proximal end of the distal tip 34. The struts 36 can also be in the form of elongate bars or tubes, or alternatively they can be formed from an elongate extension of a portion of the outer shaft 14, rather than a separate element. The struts 36 can have a length that is sufficient to create an open region 38 having a size that allows access to the inner wall 28 of a body lumen 12, as will be discussed in more detail below. In many applications the struts 36 can be generally rigid or semi-rigid, or alternatively the struts 36 can flex or move relative to the outer shaft 14 and/or distal tip 34, for instance to facilitate insertion through a tortuous pathway, and/or to provide a control or steering function at the distal tip 34. The distal tip 34 need not be permanently attached to the struts 36, as the distal tip 34 could be removable or interchangeable with distal tips 34 of other shapes and sizes. In use the struts 36 can generally provide support to the distal tip 34, however, in some applications the struts 36 can additionally or alternatively transmit a suction force from the inner lumen 46 of the outer shaft 14 to the seal 40 on the distal tip 34, as will be discussed in more detail below. In such a case, one or more struts 36 can be hollow or have an inner lumen formed therein. Additionally, the struts 36 may carry an antiseptic fluid or other substance, in which case the struts 36 can also include perforations or openings to deliver the antiseptic fluid to the open region 38.

Figure 6:
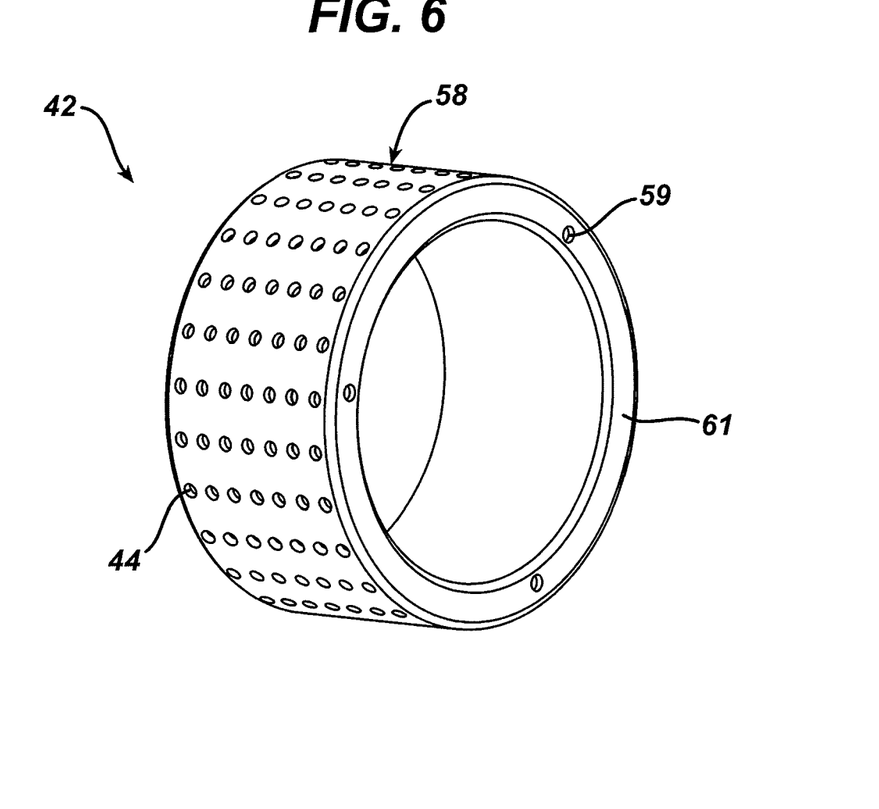
FIG. 6 is a perspective view of a second seal formed on the distal end of the outer shaft of the device shown in FIGS. 1 and 2.

As previously indicated, the device 10 can also include one or more seals 40, 42 formed thereon for isolating a section of a body lumen 12. In an exemplary embodiment, as shown in FIGS. 2, 4 and 6, the device includes a first seal 42 formed on the distal end 18 of the outer shaft 14 and a second seal 40 formed on the distal tip 34. The first and second seals 40, 42 can be effective to engage the inner walls 28 of the body lumen 12 located adjacent to the open region 38, thereby allowing the region to be isolated and optionally sterilized prior to gaining access to a body cavity positioned adjacent to the body lumen 12, as will be discussed in more detail below. The seals 40, 42 can be separate elements, as shown in FIG. 6, that are adapted to mate with the distal tip 34 or the distal end 28 of the outer shaft 14, e.g., attached as a sleeve fitting around the outer circumference of the distal end 18 of the outer shaft 14, or attached longitudinally onto the distal end 18 of the outer shaft 14 or the distal tip 34. The seals 40, 42 can also be integrally formed on the distal tip 34 or outer shaft 14 itself as a raised annular band or series of bands or region defined by the location of the suction ports 44.

While various techniques can be used to isolate a region of a body lumen 12, in the illustrated embodiment each seal 40, 42 has a generally annular shape such that they are adapted to engage tissue disposed around an outer perimeter thereof. Thus, as shown in FIGS. 4 and 6 the seals 40, 42 have a circular-cross section with an open interior. However, the seals 40, 42 can also have a oval, elliptical, square, rectangular or other cross-sectional shape and/or can have a closed interior. The seals 40, 42 can also have virtually any size. In some cases, the diameter of the seals 40, 42 can approximate or match the diameter of the outer shaft 14 or the inner diameter of the body lumen 12, and the width can be sized to provide space for additional or fewer suction ports 44, as will be discussed below. The surfaces of the seals 40, 42 can also have surface textures or features formed thereon, including a smooth, dimpled, or ridged surface. As indicated above, in an exemplary embodiment the exterior surfaces 58 of the seals 40, 42 can include one or more openings, passageways, or perforations formed therein which, as shown in FIGS. 4, 6, are in the form of suction ports 44. A wide array of suction port shapes such as holes, annular channels or cutouts, and so forth, may be employed. The end surfaces 61 of the seals 40, 42 can include a further opening or passageway 59 which can be in communication with the suction ports 44. Opening 59 can be coupled to a strut 36 or a tube extending through the outer shaft 14 and outside of the body to a source of suction, such as a vacuum mechanism, for delivering a suction force.

If the seals 40, 42 include suction ports 44, as shown in FIGS. 4 and 6, a suction force driven by an external source, such as a vacuum mechanism or pump may be provided to the suction ports 44 in the seals 40, 42. The suction force is preferably sufficient to pull tissue toward the seal, thereby engaging the body lumen 12 to create a barrier between the region of the body lumen 12 disposed between the seals 40, 42 and the remainder of the body lumen 12. Ideally, the isolating seal can act as a barrier to prevent the flow of fluids, bacteria, organic material or other potentially contaminating agents across the seal. The suction force on the inner wall 28 of the body lumen 12 can also act as stabilizing force, that is, by reducing or eliminating the ability of the outer shaft 14 and/or distal tip 34 to shift or move relative to the inner wall 28 of the body lumen 12. In this respect, the size and shape of the suction ports 44 can have a varying effect on the suction force required and the efficacy of the seal against soft tissue.

While the illustrated embodiment includes suction ports 44, the seals 40, 42 can be effective to create an isolating seal in a variety of ways. In other embodiments, the exterior surfaces 58 of seals 40, 42 may form an interference fit with the body lumen 12, excrete a sealing substance or compound, or include an expandable member which is inflated and/or expanded against the inner wall 28 of the body lumen 12. The expandable member can have virtually any expansion mechanism, such as gas or fluid-filled bladder, mechanical expanders or sleeves, electromagnetic sources, etc. It should be noted that while the seals 40, 42 have been discussed together, it will be recognized by one of ordinary skill in the art that the seals 40, 42 need not be identical and can differ in any or all of the above aspects.

As previously discussed, the device 10 can also include a hollow inner shaft 23 disposed through the outer shaft 14 and adapted to provide access for surgical materials and tools from outside the body to the isolated section of the body lumen 12. While the inner shaft 23 can have a variety of configurations, in the illustrated embodiment the inner shaft 23 has a proximal end 24 mated to the distal end 18 of the outer shaft 14 and a distal end 26 positioned between the seals 40, 42 and within the open region 38 of the outer shaft 14. In other embodiments the inner shaft can extend through the entire length of the outer shaft 14. The inner shaft 23 can also optionally be fixed, slidably, and/or rotatably movable with respect to the outer shaft 14.

Figure 7:
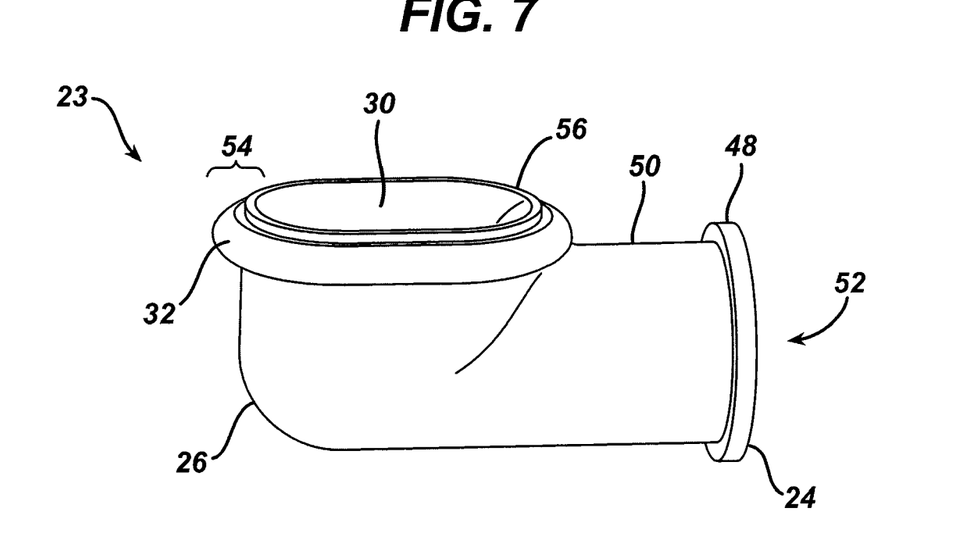
FIG. 7 is a side view of an inner shaft of the device shown in FIGS. 1 and 2.

As further shown in FIG. 7 the inner shaft 23 can also include an access port or opening 30 formed therein for providing access to or exposure to an inner wall 28 of the body lumen 12 containing the inner shaft 23. In an exemplary embodiment, the opening 30 is formed in a sidewall 50 of the inner shaft 23 and is oriented transversely or at an angle relative to a longitudinal axis of the inner shaft 23 to provide lateral access to an adjacent inner wall 28 of the body lumen 12, as depicted in FIGS. 1-2. Alternatively, the opening 30 can be formed in a distal wall or distal end 26 of the inner shaft 23 instead of on the sidewall 50. More than one opening 30 can also be included, for instance to provide multiple access points to an inner wall 28 of the body lumen 12. The opening 30 can be virtually any size and shape, including circular, oval, elliptical, square, rectangular, triangular, and so on. The opening 30 can also be shaped to contour the inner wall 28 of the body lumen 12, e.g., a concave, convex, cup-shaped, or virtually any other shape. In the illustrated embodiment the opening 30 is generally oval, which can be advantageous in some applications because it provides a larger opening in a longitudinal direction in which to manipulate and/or operate instruments extending from the interior 52 of the inner shaft 23 and through the opening 30. The inner shaft 23 can also be formed of any variety of materials, and can be rigid or stiff, or alternatively it can be flexible or semi-flexible to allow the inner shaft 23 to bend and deform as the surgeon advances an instrument through the opening 30.

The opening 30 can also optionally include an expandable member 32 disposed therearound for stabilizing a perimeter 56 of the opening 30 relative to the inner wall 28. The expandable member 32 can have any number of forms, such as an inflatable bladder that is capable of being filled with a fluid or gas injected from the exterior of the device 10 either before or during a procedure, although the bladder may also be prefabricated with or supplied in an inflated or semi-inflated state. Alternatively, the expandable member 32 can have a fixed shape and size rather than being inflatable, yet it may still be pliable or flexible. For example, the expandable member 32 can be made of rubber, foam, or other materials. In some cases, the stabilizing member can be in the form of a flange formed around the opening 30 of the inner shaft 23 and made of the same or similar material as the inner shaft 23. In use, the expandable member 32 can increase the width 54 of the perimeter 56 of the opening 30 to improve stability and contact with the inner wall 28 of the body lumen 12.

One skilled in the art will appreciate that the access device 10 shown in FIGS. 3-7 can have a variety of other configurations. For example, the arrangement shown in FIGS. 1 and 2 can be modified to include multiple openings, cutouts, ports, etc., providing multiple access points to the inner wall 28 of the body lumen 12 along the length of the inner shaft 23 and/or outer shaft 14, potentially providing multiple points of access to a body cavity. Such modifications can involve additional seals 40, 42 and/or additional open regions 38 along other portions of the outer shaft 14, resulting in the ability to isolate multiple section of the body lumen 12. In another variation, the expandable member 32 disposed around the opening 30 of the inner shaft 23 can be replaced with a seal having suction ports 44 similar to those described with respect to FIGS. 4 and 6. Additionally, the inner shaft 23 or the outer shaft 14 can be omitted and the remaining shaft can include a distal seal 40, a proximal seal 42, and an opening 30 disposed between the seals 40, 42 adapted to provide access to an adjacent inner wall 28 of the body lumen 12. The integration of irrigation devices, optical viewing instruments, energy delivery tools, surgical instruments, and other known apparatus are also contemplated and within the scope of this disclosure.

The present invention also provides methods for accessing a body cavity via a body lumen. In an exemplary embodiment, the methods allow a region of a body lumen to be isolated and sterilized to provide sterile access to a body cavity located adjacent to the body lumen. In one exemplary method, an access device, such as the device 10 shown in FIG. 1, can be inserted into a natural orifice such as the mouth or anus and through a body lumen 12 such as the colon. The opening 30 of the device 10 can be positioned adjacent to a wall 28 of the body lumen 12 to be penetrated to gain access to a body cavity, such as the peritoneal cavity. This insertion and/or placement may be associated with or preceded by any number of procedures to lubricate, flex, shape, measure, steer, turn, rotate, and/or guide the advancing distal tip 34, inner shaft 23, and/or outer shaft 14 into and within the body lumen 12. In addition, the insertion process may itself include stages: the distal tip 34 and outer shaft 14 of FIG. 1 can be inserted and advanced, then the inner shaft 23 can be inserted and advanced through the inner lumen 46 in the outer shaft 14, and so on. The insertion may also be assisted by or performed with an optical viewing instrument or endoscopic device for showing the path of the distal tip 34 or showing the inner wall 28 of the lumen adjacent to the opening 30 of the inner shaft 23.

To isolate a section of the body lumen 12 containing the opening 30 of the inner shaft 23, the first seal 40 located distal to the opening 30 of the inner shaft 23 and the second seal 42 located proximal to the opening 30 of the inner shaft 23 can be used to engage the body lumen 12. For example, a suction force can be applied to the first and second seals 40, 42, e.g., by activating a vacuum mechanism connected to the suction ports 44 of the first and second seals 40, 42. The suction force should be sufficiently strong to form a seal by suctioning tissue (that is, the inner wall 28 of the body lumen 12 disposed around the seals 40, 42) onto the first and second seals 40, 42, creating a barrier that is ideally fluid-tight. As a result, the portion of the lumen positioned between the seals 40, 42 will be isolated from the remainder of the body lumen 12.

In many applications it may be desirable to sterilize the isolated section of the body lumen 12. One suitable technique, for example, includes delivering saline or an antiseptic agent to the isolated section, for example through the inner shaft 23, through the inner lumen 46 in the outer shaft 14, or through one or more of the hollow struts 36, in order to rinse the isolated section. After an appropriate degree of rinsing or cleansing, the surgeon may evacuate the antiseptic agent from the isolated section, for example by suctioning it back through the inner shaft 23, or the outer shaft 14, etc. Sterilizing the isolated section of the body lumen 12 will prevent bacteria from entering the body cavity accessed via the isolated section of the body lumen 12.

In order to create a passageway through the inner wall 28 of the body lumen 12, the opening 30 in the inner shaft 23 can be placed against the inner wall 28 of the body lumen 12. The surgeon can optionally inflate or otherwise expand the expandable member 32 to aid in stabilizing the placement of the opening 30, if it has not been done beforehand. Any number of known surgical techniques can be used to penetrate the body lumen 12. For example, various surgical cutting, otomizing, piercing tools, or other devices can be inserted through the outer shaft 14 and/or the inner shaft 23 and through the opening 30 and used to puncture or cut the body lumen 12 to gain access to the body cavity. If the inner shaft 23 is not employed, penetration through the inner wall 28 of the body lumen 12 can occur between the struts 36 in the open region 38 where the inner lumen wall 28 of the body lumen 12 is exposed.

Additional aspects of the surgical procedure which will be apparent to one skill in the art may include the insertion of surgical instruments and materials into a body cavity through the inner lumen wall 28, insufflating or tenting a body cavity, suturing of the inner lumen wall 28, and deactivation of the suction ports 44 to release the first and second seals 40, 42, which usually will have been maintained during the procedure. The surgeon may also perform additional sterilization cycles and eventually can withdraw the instrument from the body lumen 12.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning and/or replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. It is preferred that the device is sterilized. This can be done by any number of ways known to those skilled in the art including beta or gamma radiation, ethylene oxide, or steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A translumenal access device, comprising:
    an inner shaft adapted to be inserted through a body lumen and having proximal and distal ends with an inner lumen extending therethrough, the distal end including an opening adapted to be positioned adjacent to an inner wall of a body lumen containing the inner shaft; and
    an outer shaft disposed around at least a portion of the inner shaft;
    a sealing mechanism coupled to a distal portion of the outer shaft and at least partially disposed around and movable relative to the inner shaft, the sealing mechanism having a first seal positioned distal of the opening and a second seal positioned proximal of the opening, the first seal being formed on a distal tip coupled to the distal end of the outer shaft by one or more struts extending therebetween such that the first seal is spaced apart from a distal-most end of the outer shaft, and the second seal being disposed around the distal-most end of the outer shaft, the first and second seals each having a plurality of suction ports formed around an outer perimeter thereof and adapted to suction tissue thereon so as to form a seal around an inner wall of a body lumen and to isolate the opening in the inner shaft within a portion of a body lumen.

2. The device of claim 1, wherein the first and second seals each comprises annular seals.

3. The device of claim 1, further comprising an expandable member disposed around the opening and adapted to stabilize the opening relative to a tissue surface.

4. The device of claim 1, further comprising an optical viewing instrument associated with the distal tip of the outer shaft.

5. The device of claim 1, wherein the opening is formed in a sidewall of the inner shaft.

6. The system of claim 1, wherein at least one of the struts has a lumen formed therein for transmitting a suction force to the first seal.

7. A translumenal access system, comprising:
    an outer shaft having proximal and distal ends with an inner lumen extending therethrough, the outer shaft being adapted to be inserted through a body lumen;
    an access element extending from the distal end of the outer shaft and having at least one opening formed therein and configured to be positioned adjacent to an inner wall of a body lumen;
    a first annular seal coupled to the outer shaft and positioned distal of the opening, the first annular seal being configured to engage and to form a seal with an inner wall of a body lumen; and
    a second annular seal coupled to the outer shaft and positioned proximal of the opening, the second annular seal being configured to engage and to form a seal with an inner wall of a body lumen, wherein the first and second annular seals each include a plurality of suctions ports formed around an outer perimeter thereof and adapted to suction tissue thereon, and wherein the first annular seal is formed on a distal tip coupled to the distal end of the outer shaft by one or more struts extending therebetween such that the first seal is spaced apart from a distal-most end of the outer shaft, and the second annular seal is disposed around the distal-most end of the outer shaft.

8. The system of claim 7, wherein the access element comprises an inner shaft extending through the outer shaft.

9. The system of claim 8, wherein the opening is formed in a sidewall of the inner shaft adjacent to a distal end of the inner shaft.

10. The system of claim 7, wherein the distal tip is capped to prevent fluid flow therethrough.

11. The system of claim 7, further comprising an expandable member disposed around the opening and adapted to stabilize the opening relative to a tissue surface.

12. The system of claim 7, further comprising an optical viewing instrument associated with the distal end of the outer shaft.

13. The system of claim 7, wherein at least a portion of the outer shaft and the access element are flexible to allow the outer shaft and access element to be inserted through a tortuous lumen.

14. A translumenal access system, comprising:
- an outer shaft having proximal and distal ends with an inner lumen extending therethrough, the outer shaft being adapted to be inserted through a body lumen;
- an access element extending from the distal end of the outer shaft and having at least one opening formed therein and configured to be positioned adjacent to an inner wall of a body lumen;
- an expandable member disposed around the perimeter of the opening to stabilize the opening relative to a tissue surface;
- a first annular seal formed on a distal tip coupled to the distal end of the outer shaft by one or more struts extending therebetween such that the first seal is spaced apart from the distal-most end of the outer shaft and positioned distal of the opening, the first annular seal being configured to engage and to form a seal with an inner wall of a body lumen; and
- a second annular seal coupled to the outer shaft and positioned proximal of the opening, the second annular seal being configured to engage and to form a seal with an inner wall of a body lumen.

15. The system of claim 14, wherein the access element comprises an inner shaft extending through the outer shaft.

16. The system of claim 15, wherein the opening is formed in a sidewall of the inner shaft adjacent to a distal end of the inner shaft.

17. The system of claim 14, wherein the first and second annular seals each include a plurality of suctions ports formed around an outer perimeter thereof and adapted to suction tissue onto the first and second annular seals.

18. The system of claim 14, wherein the first annular seal is formed on a distal tip coupled to and spaced apart from the distal-most end of the outer shaft, and the second annular seal is disposed around the distal-most end of the outer shaft.

19. The system of claim 17, wherein the distal tip is capped to prevent fluid flow therethrough.

20. The system of claim 14, further comprising an optical viewing instrument associated with the distal end of the outer shaft.

21. The system of claim 14, wherein at least a portion of the outer shaft and the access element are flexible to allow the outer shaft and access element to be inserted through a tortuous lumen.

* * * * *